(12) United States Patent
Lipchak

(10) Patent No.: US 11,110,002 B2
(45) Date of Patent: Sep. 7, 2021

(54) DEVICE FOR FACILITATING INTRODUCTION OF MEDICINAL DROPS INTO THE EYES AND METHODS OF USE

(71) Applicant: John Lipchak, Matawan, NJ (US)

(72) Inventor: John Lipchak, Matawan, NJ (US)

( * ) Notice: Subject to any disclaimer, the term of this patent is extended or adjusted under 35 U.S.C. 154(b) by 347 days.

(21) Appl. No.: 16/297,812

(22) Filed: Mar. 11, 2019

(65) Prior Publication Data

US 2019/0290486 A1 Sep. 26, 2019

Related U.S. Application Data

(60) Provisional application No. 62/648,280, filed on Mar. 26, 2018.

(51) Int. Cl.
*A61F 9/00* (2006.01)

(52) U.S. Cl.
CPC ...... *A61F 9/0026* (2013.01); *A61F 2240/001* (2013.01)

(58) Field of Classification Search
CPC ...... A61F 9/00; A61F 9/0026; A61F 2240/00; A61F 2240/001
USPC ......................................................... 604/305
See application file for complete search history.

(56) References Cited

U.S. PATENT DOCUMENTS

| | | | |
|---|---|---|---|
| 1,959,915 A * | 5/1934 | Guthrie .................. | G02C 7/165 351/46 |
| 3,446,209 A | 5/1969 | Macha | |
| 4,183,355 A | 1/1980 | Meckler | |
| 4,468,103 A * | 8/1984 | Meckler ................ | A61F 9/0026 351/158 |
| 4,531,944 A | 7/1985 | Bechtle | |
| 4,872,217 A * | 10/1989 | Kitayama ................ | A61F 9/04 2/15 |
| 5,255,024 A | 10/1993 | Jensen | |
| 5,569,224 A | 10/1996 | Michalos | |
| 7,784,934 B2 * | 8/2010 | Gauger .................... | G02C 7/16 351/45 |
| 8,486,031 B2 | 7/2013 | Bogdan | |
| 2014/0094759 A1 | 4/2014 | Mansfield | |
| 2017/0151735 A1 | 6/2017 | He | |
| 2017/0160561 A1 | 6/2017 | He | |
| 2020/0393703 A1 * | 12/2020 | McMillian ............. | G02C 7/165 |

FOREIGN PATENT DOCUMENTS

FR     2635011 A1    2/1990

OTHER PUBLICATIONS

Melvin I. Freeman, Section of Ophthalmology, The Mason Clinic, Virginia Mason Research Center, Seattle, Scientific Poster Presentation at 1978 Annual Meeting of the American Academy of Ophthalmology, Kansas City, MO, Oct. 22-26). (Year: 1978).*

* cited by examiner

*Primary Examiner* — Tatyana Zalukaeva
*Assistant Examiner* — Meagan Ngo
(74) *Attorney, Agent, or Firm* — Wei & Sleman LLP

(57) ABSTRACT

An eye drop guide includes a frame including at least one eye-covering member, and a plurality of apertures arranged in columns, each column having multiple apertures, the apertures in each column being vertically offset from apertures in adjacent columns.

18 Claims, 5 Drawing Sheets

DEVICE FOR FACILITATING INTRODUCTION OF MEDICINAL DROPS INTO THE EYES AND METHODS OF USE

CROSS-REFERENCE TO RELATED APPLICATIONS

The present invention claims priority to U.S. Provisional Application Ser. No. 62/648,280, entitled "DEVICE FOR FACILITATING INTRODUCTION OF MEDICINAL DROPS INTO THE EYES AND METHODS OF USE," filed Mar. 26, 2018, which is incorporated by reference herein in its entirety.

FIELD OF THE DISCLOSURE

The present invention relates to the application of eye drops, and, more particularly, to an eye drop application aid for self-application of droplets of ophthalmic solution by an individual, or application by an assistant.

BACKGROUND OF THE DISCLOSURE

Eye drops are used to care and treat a variety of conditions. Such eye drops may include prescription and non-prescription drops formulated to alleviate conditions ranging from simple eye strain, or dry eyes to more serious diseases, such as glaucoma. Generally, eye drops are supplied to the user either in a bottle with a conventional medicine dropper type of cap or in a soft-sided squeeze bottle having a nozzle with a discharge opening. A user will typically hold the end of the medicine dropper or the bottle nozzle over the eye and squeeze the medicine dropper bulb or squeeze bottle sides to discharge droplets of the solution into the eyes.

In some cases, a patient may prefer to self-administer eye drops, for example, because they are afraid of being injured by another person. Because most eye drops are self-administered, one or more problems may occur. For example, some users or patients may have tremors that makes it difficult to dispense the eye drops in the correct location. Other users or patients may lack the coordination necessary to aim the bottle or dropper, missing the eye and wasting medication and causing frustration that may lead to non-compliance with doctor instructions. Still, other users may focus on centering the device, and accidently contact their eyes, injuring themselves.

Because of the frequent problems with self-administration of eye drops, a wide variety of devices have been developed over the years to facilitate the self-administration of eye drops. Structures ranging from complex dispensers to a variety of dispenser alignment supports have been proposed with varying degrees of success.

However, most of these devices are unnecessarily complex and expensive to manufacture. Yet another problem with most of the prior art devices is that they are designed to be usable only with a particular patient, and do not successfully take into account the variations in patient head sizes or anthropometric data, such as distances between the eyes. Moreover, some devices force the user to place a drop at the center of the eye, when the user would rather introduce the eye drops at another location on the eye or with the eyelid closed.

SUMMARY OF THE DISCLOSURE

In some embodiments, an eye drop guide includes a frame having at least one eye-covering member, and a plurality of apertures arranged in columns, each column having multiple apertures, the apertures in each column being vertically offset from apertures in adjacent columns.

In some embodiments, an eye drop guide includes a frame including at least one eye-covering member, and a plurality of apertures arranged in columns, each column having multiple apertures, wherein apertures in a selected column are in communication with other apertures in the selected column.

BRIEF DESCRIPTION OF THE DISCLOSURE

Various embodiments of the presently disclosed connectors are disclosed herein with reference to the drawings, wherein.

Various embodiments of the present invention will now be described with reference to the appended drawings. It is to be appreciated that these drawings depict only some embodiments of the invention and are therefore not to be considered limiting of its scope.

DETAILED DESCRIPTION

Despite the various improvements that have been made to eye drop applicators, conventional methods suffer from some shortcomings as discussed above.

There therefore is a need for further improvements to the devices and methods used to facilitate the introduction of eye drops to the eyes. Among other advantages, the present disclosure may address one or more of these needs.

Figure 1:
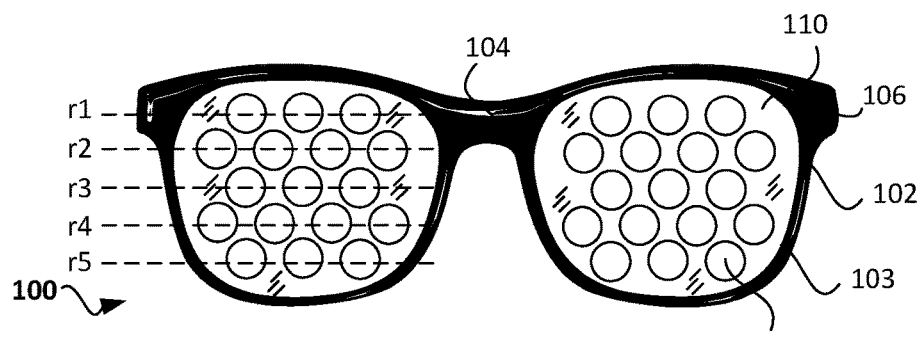
FIG. 1 is a schematic front view of an eye drop guide having lenses and a plurality of apertures according to one embodiment.

FIG. 1 shows an eye drop guide 100, generally shaped like a pair of eyeglasses. Eye drop guide 100 may include a metallic or plastic frame 102 having a pair of substantially circular portions 103 coupled together via nose bridge 104, the portions 103 being also coupled to temples or arms 106. In some examples, frame 102 may be approximately 5 inches in width, and approximately 2 inches in height. A hinge 105 may be disposed between each of portions 103 and temples 106 so that the temples may be folded toward the portions 103.

Each circular portion 103 may house, or otherwise be coupled to, a plastic or polycarbonate lens 110. As shown in FIG. 1, lens 110 includes a number of circular apertures 112 that extend there through from one side to the other. Specifically, apertures 112 are disposed in a predetermined honeycomb pattern—that is, they are arranged in a number of rows and columns, apertures in each row being offset from apertures in adjacent rows. Each row may include the same number of apertures 122, or may include a different number of apertures. As shown, alternating rows include the same number of apertures 112. Additionally, each row is offset from the rows above and/or below it, and alternating rows are generally aligned with one another. In the embodiment shown, five rows are shown, and rows r1, r3, and r5 includes the same number of apertures, e.g., three apertures, and are aligned with one another. Rows r2, and r4 include the same number of apertures, e.g., four apertures and are also aligned with one another, but offset from rows r1, r3 and r5.

Each of the apertures may be wide enough to accept the tip of an eye dropper or a nozzle of a bottle. Thus, apertures 112 may have a diameter in the range of 3/16 to 3/8 inches. It will be understood that although circular apertures are shown, apertures of different shapes and sizes, such as oval, triangular, square, pentagon, etc. may also be utilized. Additionally, the exact locations of the apertures may be modified. For example, certain patients prefer that the eye drop fall directly in the center of the eye. Others would rather pull down gently on skin slightly below the eye, and create a pocket between the lower eyelid and the eyeball, and introduce the eye drops into the pocket. Additionally, some users may prefer to place the drop in the corner of the eye towards the nose (nasal caruncle) with the eye closed and let gravity pull the drop into the eye by blinking. Additionally, because patients have different head sizes, and the spacing between patients' eyes differ, eye drop guide 100 provides a number of options, and allows the user the ability to choose where they would rather place the drops (e.g., through an aperture at the center of the eyes, through an aperture closer to the upper eyelid, through an aperture closer to the bottom eyelid, or through an aperture that is disposed near one of the sides of the eye.

Figure 2:
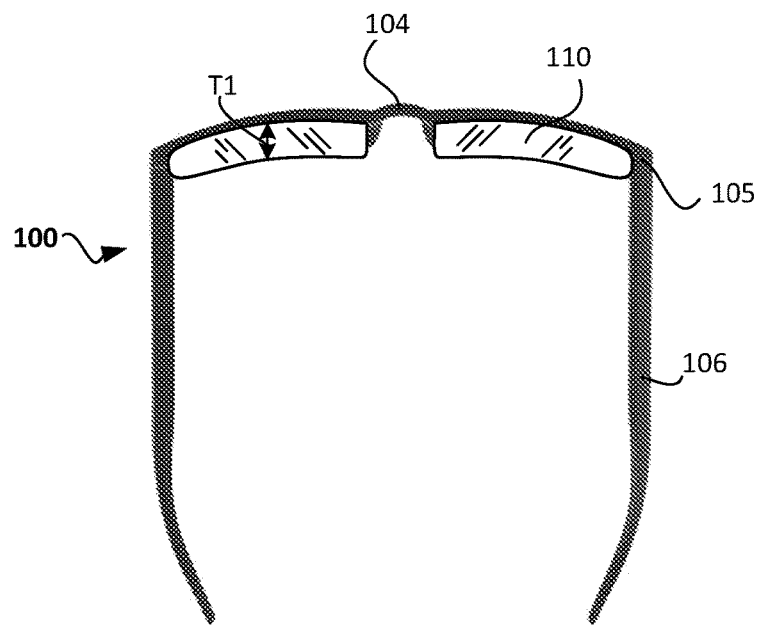
FIG. 2 is a schematic top view of the eye drop guide of FIG. 1.

FIG. 2 is a schematic top view of the eye drop guide 100 of FIG. 1. As shown, lenses 110 are intentionally thicker than traditional lenses. Specifically, lenses 110 may have a thickness T that is between 0.25 inches and 2 inches. In at least some examples, lenses 110 have a thickness of at least 0.25 inches.

Figure 3A:
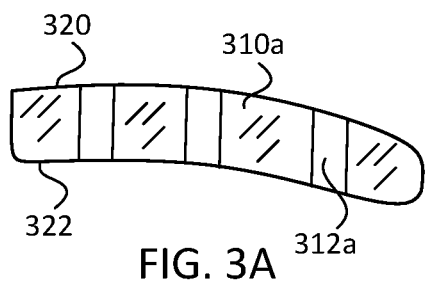
FIG. 3A is an enlarged schematic cross-sectional view of a lens having cylindrical apertures for use with the eye drop guide.
Figure 3B:
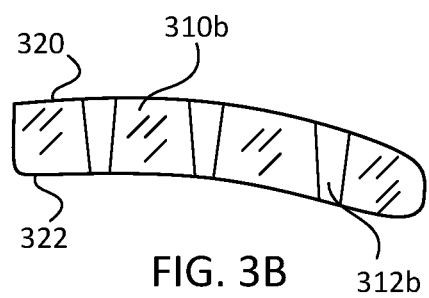
FIG. 3B is an enlarged schematic cross-sectional view of another lens having frustoconical apertures for use with the eye drop guide.

A close-up view of some examples of the lenses that are possible are shown in the cross-sections of FIGS. 3A and 3B. As shown in FIG. 3A, lens 310a includes generally tubular or cylindrical apertures 312a that pass from the outer surface 320 of the lens (e.g., the surface that faces away from the patient) to the inner surface 322 of the lens (e.g., the surface that faces the patient's eyes). That is, the diameter of the apertures 312a are constant from one surface to the other. Though the lens are shown as being concave, it will be understood that a rectangular, flat lens may be used instead.

Conversely, FIG. 3B illustrates a lens 310b that includes frustoconical apertures 312b that pass from the outer surface 320 of the lens (e.g., the surface that faces away from the patient) to the inner surface 322 of the lens (e.g., the surface that faces the patient's eyes). That is, the diameter of the apertures 312b gradually decreases from the outer surface 320 to the inner surface 322. In such an embodiment, the diameter of the aperture may decrease from a maximum diameter of between 3/16 and 3/8 inches to a minimum diameter of between 1/16 and 5/16 inches.

In use, the patient may wear eye drop guide 100 as they would a pair of eyeglasses. The patient may then take an eye dropper or squeezable bottle and select one of the many apertures that are disposed in a lens of the eye drop guide 100, and align the nozzle with the selected aperture. The patient would then lie down with their head facing the ceiling and place the eye drop guide (with dropper bottle tip already through the appropriate hole) on their face as they would a normal pair of glasses. The patient may then squeeze the dropper or bottle, and introduce the drops to the eye at the desired location (e.g., at the center of the eye, near the pocket of the lower eyelid, or near the upper eyelid, or to one side of the eyes). The eye drop guide may be used for drop insertion and removed thereafter so not to block the patient's vision.

Figure 4:
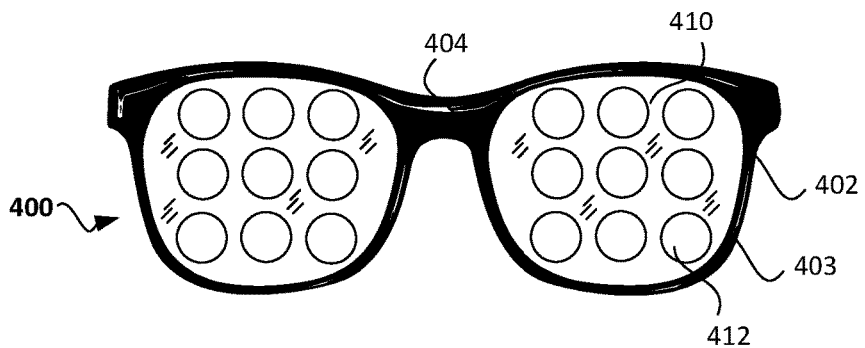
FIG. 4 is a schematic front view of an eye drop guide having aligned apertures according to another embodiment.
Figure 5:
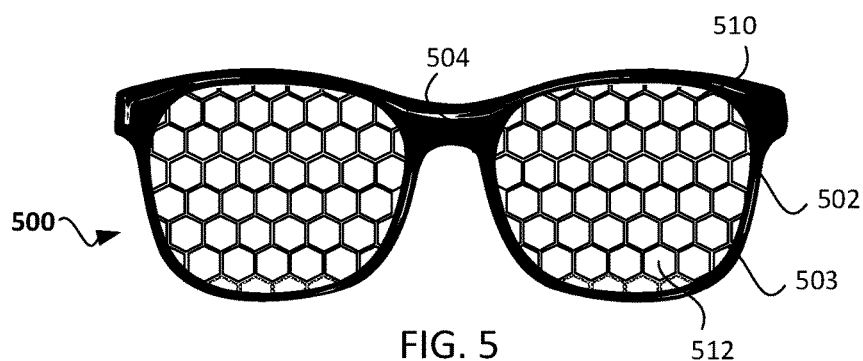
FIG. 5 is a schematic front view of an eye drop guide having hexagonal apertures according to another embodiment.

FIGS. 4 and 5 illustrate two additional variations. In FIG. 4, eye drop guide 400 includes a frame 402 having circular portions 403 housing a pair of lenses 410. One main difference between the embodiment of FIG. 4 and that of FIG. 1 is the number and location of apertures. FIG. 4 shows a lens having apertures 412 arranged in a 3×3 orientation (i.e., three rows by three columns). In this example, each row includes three apertures, and each column includes three apertures. Additionally, the apertures of each row are aligned with apertures of subsequent rows, and the columns are similarly aligned. Apertures 412 are also slightly larger than those of FIG. 1, each aperture measuring 1/8 to 7/16 inches in diameter.

Another example is shown in FIG. 5, in which eye drop guide 500 includes a frame 502 having circular portions 503 housing a pair of lenses 510. Lens 510 includes hexagonal-shaped apertures 512 arranged in a honeycomb configuration, in which each aperture shares ones of its sides with a neighboring apertures, so that each aperture is surrounded by six other apertures unless that aperture falls near the periphery of the lens. In some embodiments, the maximum diagonal of each hexagon is equal to 3/16 to 3/8 inches.

Figure 6:
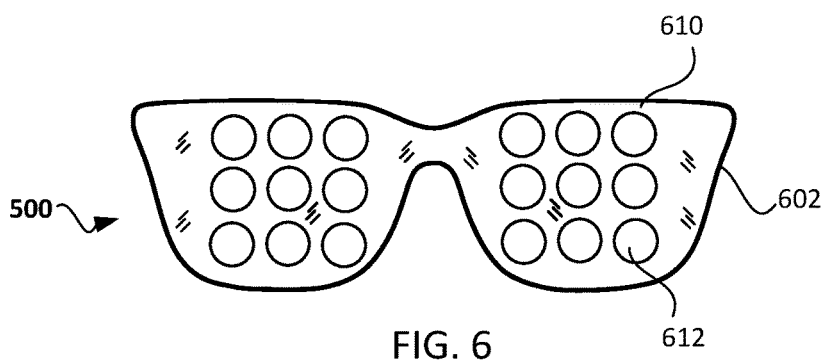
FIG. 6 is a schematic front view of an eye drop guide according to another embodiment.

FIG. 6 illustrates another variation in which eye guide 600 is formed unitarily. Specifically, eye drop guide 600 includes a unitary frame 602 and lenses 610, which are formed of a plastic or polymer. That is, instead of having a separate frame that is capable of accepting lenses, the entire device may be formed of a single piece of material (e.g., plastic). Bendable temples or arms may be added to the device so that it rests on the patient's or user's ears. The unitary frame and lenses may be moulded or otherwise formed together in a variety of ways. The unitary frame/glasses may include a color, and/or may be translucent. A number of apertures 612 arranged in a 3×3 orientation (i.e., three rows by three columns) are drilled or otherwise formed in the eye drop guide 600.

7A-G are schematic outside and inside perspective views, front, back, top, bottom, and side views of an eye drop guide according to another embodiment. Eye drop guide 700 may include a frame 702 having two symmetric halves, each half forming an eye-covering member 703 coupled to a clasp 705 on one end for coupling to a band or elastic strap (not shown) and further being coupled to the other eye-covering member via a nose bridge 704. In at least some examples, the two eye-covering members may be separable and coupleable to one another. Each eye-covering member 703 may be substantially flat as shown, and may include a plurality of apertures 712 arranged in clusters 711. In at least some example, a guide may be formed with only one eye-covering member 703 having a cluster of apertures.

Figure 7A:
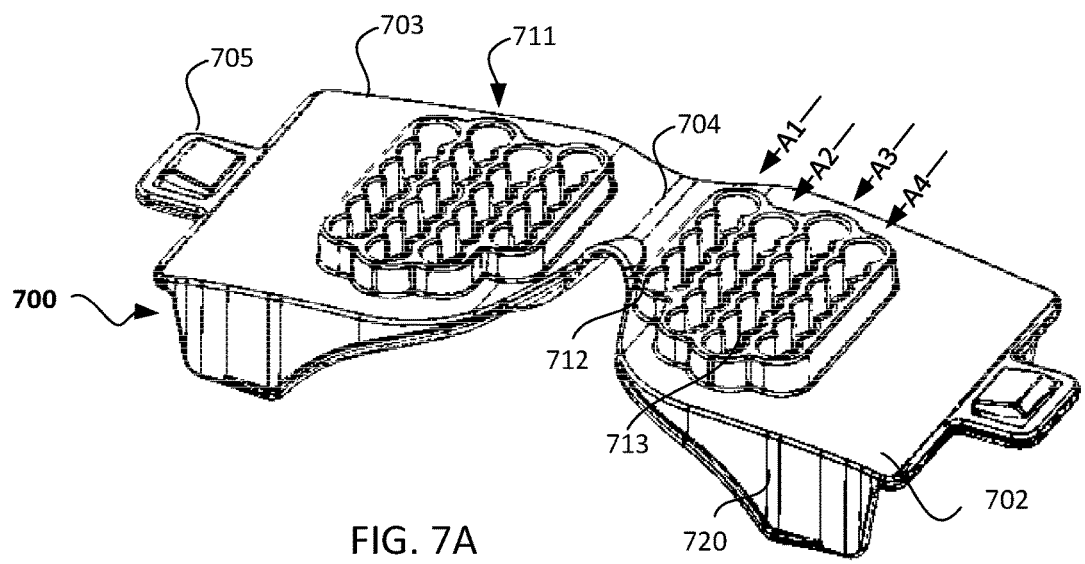
FIGS. 7A-G are schematic outside and inside perspective views, front, back, top, bottom, and side views of an eye drop guide according to another embodiment.
Figure 7B:
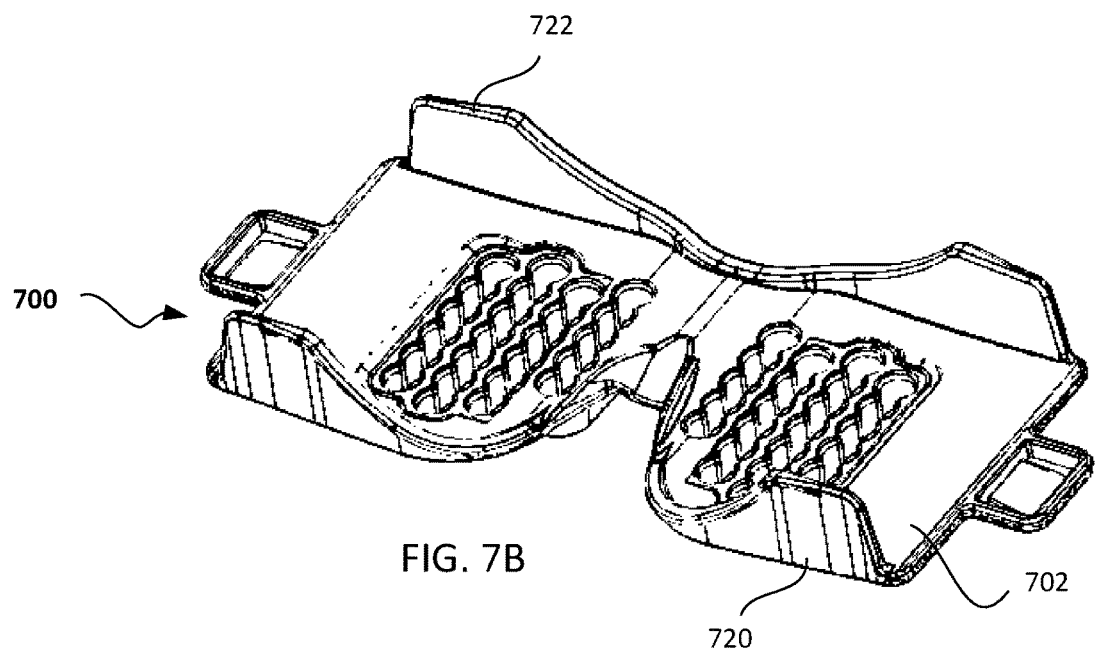
Figure 7C:
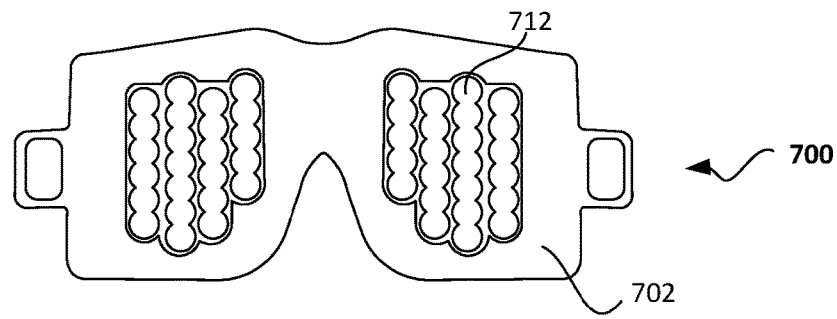
Figure 7D:
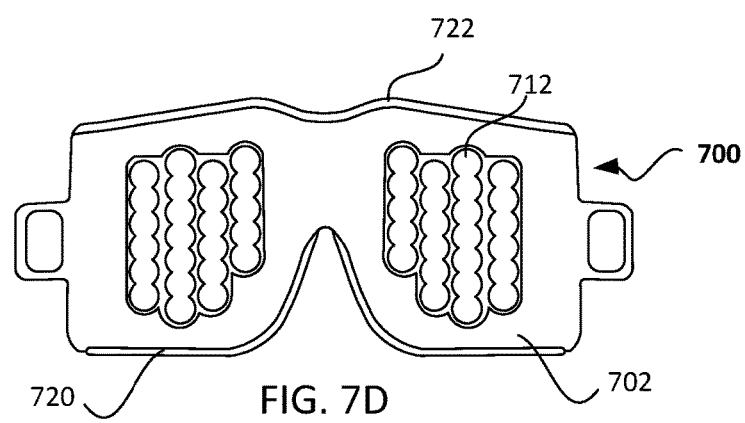
Figure 7E:
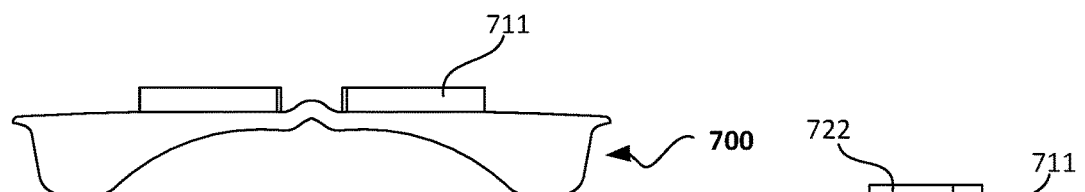
Figure 7F:
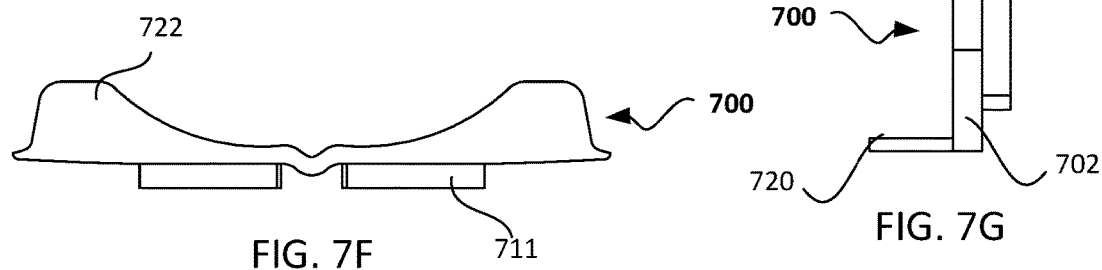
Figure 7G:
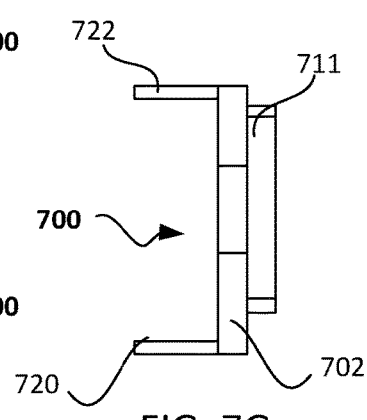

Each aperture 712 may be substantially cylindrical and may have a diameter in the range of 1/8 to 3/8 inches. Alternatively, the apertures 712 may be slightly tapered from a largest uppermost diameter (located furthest from the eye), to a smallest lowermost diameter (located closest to the eye). By cylindrical, it is meant that the apertures 712 are also formed as wells having sidewalls with a predetermined height. For example, in some examples, the wells have a height of ⅛ to ½ inch measured from the eye-covering member 703 to the top of the aperture as shown in FIG. 7A. This height may be advantageous for securing and stabilizing a bottle in place within an aperture, and for spacing the bottle away from the eye. As used herein, the term "aperture" means an opening that extends through an eye-covering member and is configured to accept a portion of, for example, a squeeze bottle. Two or more openings may be in communication with one another (e.g., lacking a sidewall that separates them). In that case, such openings may be referred to as two distinct apertures, or multiple apertures, even though they are in communication with one another and form a larger opening with an irregular shape.

As shown, apertures 712 may be arranged in columns labeled A1, A2, A3, A4. In this configuration, the apertures are arranged in four columns. Alternatively, the apertures may be arranged in two, three, five, six, or seven columns. Each column may include a different number of apertures. For example, column A1 may include 5 apertures, A2 may include 6 apertures, A3 may include 7 apertures, and A4 may include 6 apertures. As shown, adjacent columns are vertically offset from one another, and every-other column may be substantially vertically aligned (e.g., columns A1 and A3 are vertically aligned with each other and columns A2 and A4 are vertically aligned with each other). In some examples, offsetting the columns means that each aperture in a column is vertically offset by the length of half an aperture from apertures in an adjacent column. By offsetting the columns vertically in this manner, the horizontal distance between apertures in adjacent columns is reduced, and a patient may be able to locate an aperture that more accurately matches to their preferred drop introduction position. Additionally, apertures 712 in each column may be in communication with other apertures in that column so that they are connected and lack a wall separating the apertures within the column. By being "in communication" and "connected" it is meant that instead of having a fully circumferential wall, portions of the wall of each aperture is removed so that apertures are not completed separated from neighboring apertures above and/or below it. By removing the walls between apertures within a column, the vertical spacing between apertures in a column may be reduced, again leading to more accuracy in applying drops to the eyes. In some examples, a vertical barrier 713 is maintained between adjacent columns to preserve structural integrity and increase stiffness.

Finally, eye drop guide 700 includes a lower wall 720 and an upper wall 722 projecting orthogonally from frame 702. The height of lower wall may vary along its length, the height being greatest adjacent the clasps and slowly being reduced as it approaches the center adjacent nosebridge 704 to form a nose contact point. Lower wall 720 may sit adjacent the cheeks of the user. Likewise, upper wall 720 may vary in height, being greatest at the extreme ends, and slowly being reduced toward the center of the frame. Upper wall 720 may be located adjacent the forehead of the user. The profiles of upper and lower walls are selected so that the eye drop guide is comfortable for most patients.

In use, the tip of a bottle may be placed in a selected aperture of eye drop guide 700 that will align with the corner of the user's eye near their nose, and the user may let go of the bottle to ensure test its stability and/or reach within the aperture. Most bottles will stay in place in the eye drop guide 700, even when tilted. The user may then lie down flat, close their eyes and place the guide 700 on their face like a mask. The upper and lower walls of the guide will contact the user's forehead and cheeks, respectively, to create a distance between the dropper and the eye. The user may then slide the guide down their face, until it contacts their nose. By having contact with the forehead, cheeks and nose every time the device is used, proper placement may be assured. If desired, a strap may be used to keep the device in place. Keeping the eyes closed, the user may squeeze the bottle until a drop is felt on the corner of the eyelid. Without moving the head, the guide may be removed, and the user may blink four times and gravity while cause the drop to roll into the eye. The user may then close their eye again. In some applications, it is recommended that the user not blink for 1 minute afterwards.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, though a frame is shown having circular portions for accepting the lenses, it will be understood that the frame may only partially surround the lenses. Additionally, a frameless variation is contemplated where temples and a nose bridge are directly coupled to the lenses.

It will be appreciated that the various dependent claims and the features set forth therein can be combined in different ways than presented in the initial claims. It will also be appreciated that the features described in connection with individual embodiments may be shared with others of the described embodiments.

What is claimed is:

1. An eye drop guide comprising:
   a frame including at least one eye-covering member; and
   a plurality of apertures arranged in columns, each column having multiple apertures, the apertures in each column being vertically offset from apertures in adjacent columns and apertures in a selected column being in communication with other apertures in the selected column.

2. The eye drop guide of claim 1, wherein each of the apertures has a sidewall projecting from one of the eye-covering members.

3. The eye drop guide of claim 1, wherein the sidewall has a height of ¼ inch.

4. The eye drop guide of claim 1, wherein the frame is substantially flat.

5. The eye drop guide of claim 1, further including an upper wall and lower wall, each of the upper wall and the lower wall projecting from the frame.

6. The eye drop guide of claim 1, wherein each of the apertures is cylindrical.

7. The eye drop guide of claim 1, wherein each of the apertures is tapered and includes an uppermost diameter, and a lowermost diameter, the uppermost and lowermost diameters being different.

8. The eye drop guide of claim 1, each of the apertures has a diameter of ⅛ to ⅜ inches.

9. The eye drop guide of claim 1, wherein each of the columns has a different number of apertures than adjacent columns.

10. The eye drop guide of claim 1, wherein each column has one more or one fewer aperture than adjacent columns.

11. The eye drop guide of claim 1, further comprising a clasp coupled to each of the eye-covering members.

12. An eye drop guide comprising:
   a frame including at least one eye-covering member; and
   a plurality of apertures arranged in columns, each column having multiple apertures, wherein apertures in a selected column are in communication with other apertures in the selected column.

13. The eye drop guide of claim 12, wherein each of the apertures has a sidewall projecting from one of the eye-covering members.

14. The eye drop guide of claim 12, further including an upper wall and lower wall, each of the upper wall and the lower wall projecting from the frame.

15. The eye drop guide of claim 12, wherein the apertures in each column are vertically offset from apertures in adjacent columns.

16. The eye drop guide of claim 12, wherein each of the apertures is cylindrical.

17. The eye drop guide of claim 12, wherein each of the apertures is tapered and includes an uppermost diameter, and a lowermost diameter, the uppermost and lowermost diameters being different.

18. A method of manufacturing an eye drop guide, comprising:
   providing a frame including at least one eye-covering member; and
   forming a plurality of apertures arranged in columns, each column having multiple apertures, the apertures in each column being vertically offset from apertures in adjacent columns, and apertures in a selected column are in communication with other apertures in the selected column.

* * * * *